United States Patent [19]

Fujimoto

[11] Patent Number: 5,114,314
[45] Date of Patent: May 19, 1992

[54] RECIPROCATING TYPE FLUID DELIVERY PUMP

[75] Inventor: Shigeaki Fujimoto, Kyoto, Japan

[73] Assignee: Shimadzu Corporation, Kyoto, Japan

[21] Appl. No.: 574,174

[22] Filed: Aug. 29, 1990

Related U.S. Application Data

[63] Continuation-in-part of Ser. No. 255,570, Oct. 11, 1988, abandoned.

[30] Foreign Application Priority Data

Mar. 28, 1988 [JP] Japan .................................. 63-77585

[51] Int. Cl.⁵ ........................ F04B 49/06; F04B 49/08
[52] U.S. Cl. .......................................... 417/3; 417/18; 417/45; 417/199.1; 92/82; 92/87
[58] Field of Search .............. 417/3, 18, 44, 45, 199.1; 92/82, 87

[56] References Cited

U.S. PATENT DOCUMENTS

| | | | |
|---|---|---|---|
| 2,591,902 | 4/1952 | Yohpe | 92/87 |
| 4,352,636 | 10/1982 | Patterson et al. | 417/45 |
| 4,359,312 | 11/1982 | Funke et al. | 417/18 |
| 4,552,513 | 11/1985 | Miller et al. | 417/18 |
| 4,595,495 | 6/1986 | Yotam et al. | 417/18 |

Primary Examiner—Richard A. Bertsch
Assistant Examiner—David W. Scheuermann
Attorney, Agent, or Firm—Armstrong, Nikaido, Marmelstein, Kubovcik & Murray

[57] ABSTRACT

A reciprocating type fluid delivery pump has a driving motor, plungers for driving two pump heads, respectively, and a converting mechanism for converting the rotational motion of the driving motor into a reciprocating motion of each plunger. The converting mechanism includes a cam having such a configuration that, when the driving motor is rotated at constant velocity, the delivery flow rate during the delivery starting period of each of the plungers is in excess of that during the other periods of the cycle. The speed of rotation of the driving motor is reduced during the excess delivery period according to need. Thus, the load on the driving motor is reduced and it is therefore possible to employ a driving motor having a relatively low output. The delivery pump also includes a rinsing chamber for each plunger for allowing pressurized fluid to pass therethrough. The rinse chamber includes a rinse pump which uses the reciprocal movement of the pump piston for the rinse mechanism.

5 Claims, 7 Drawing Sheets

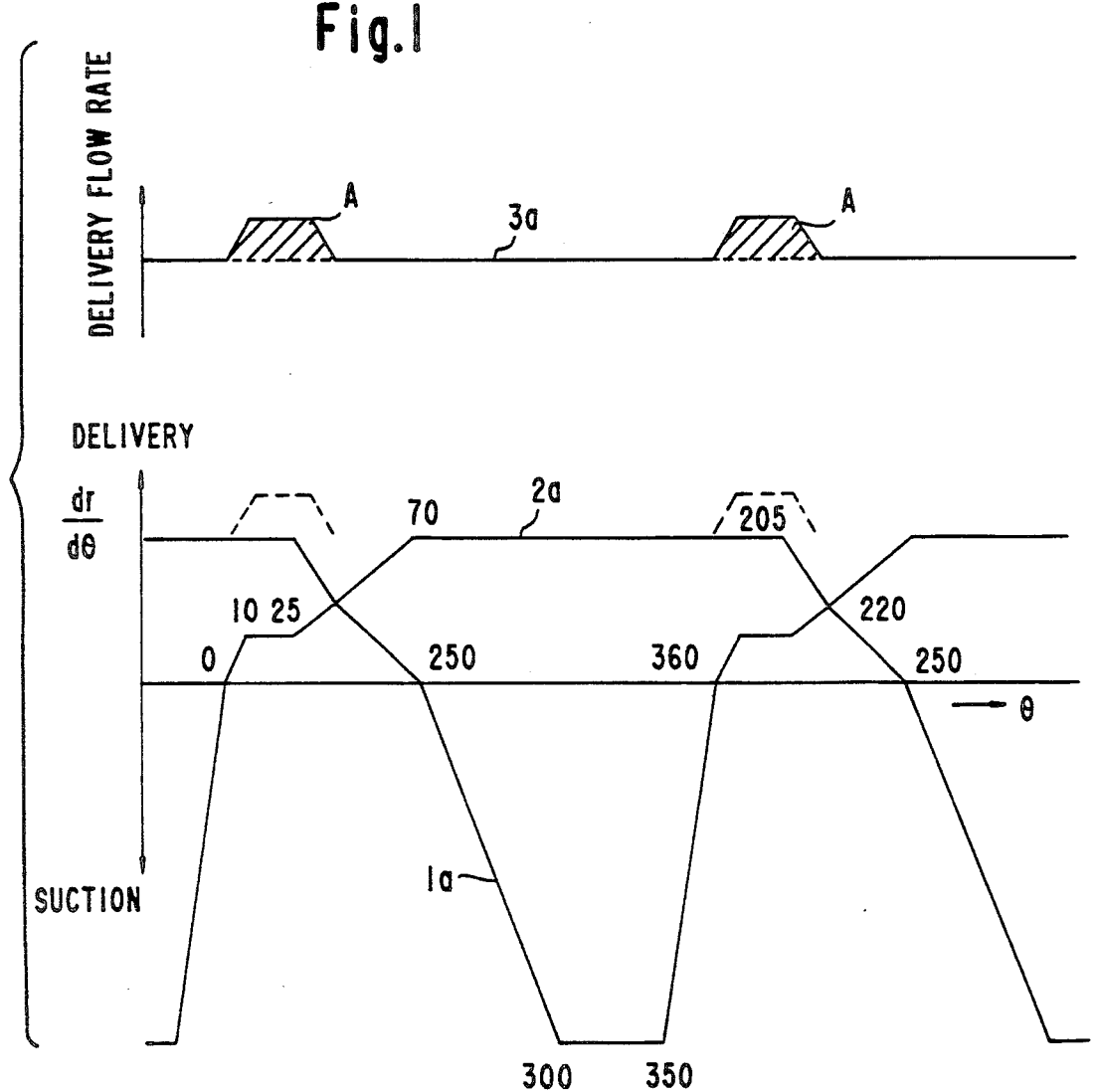
 
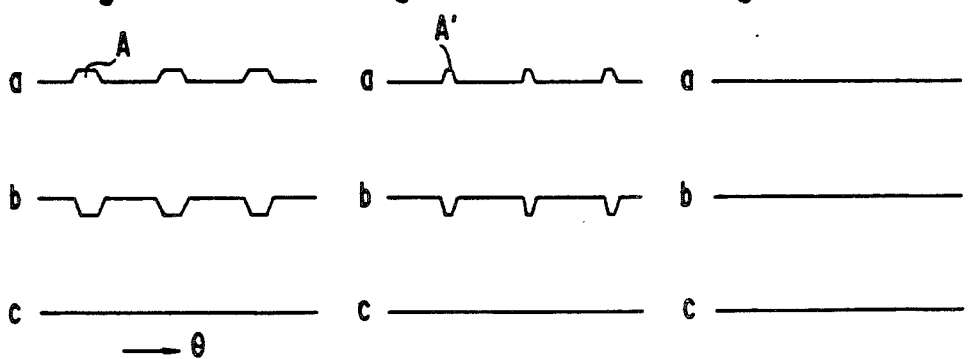

Fig.10
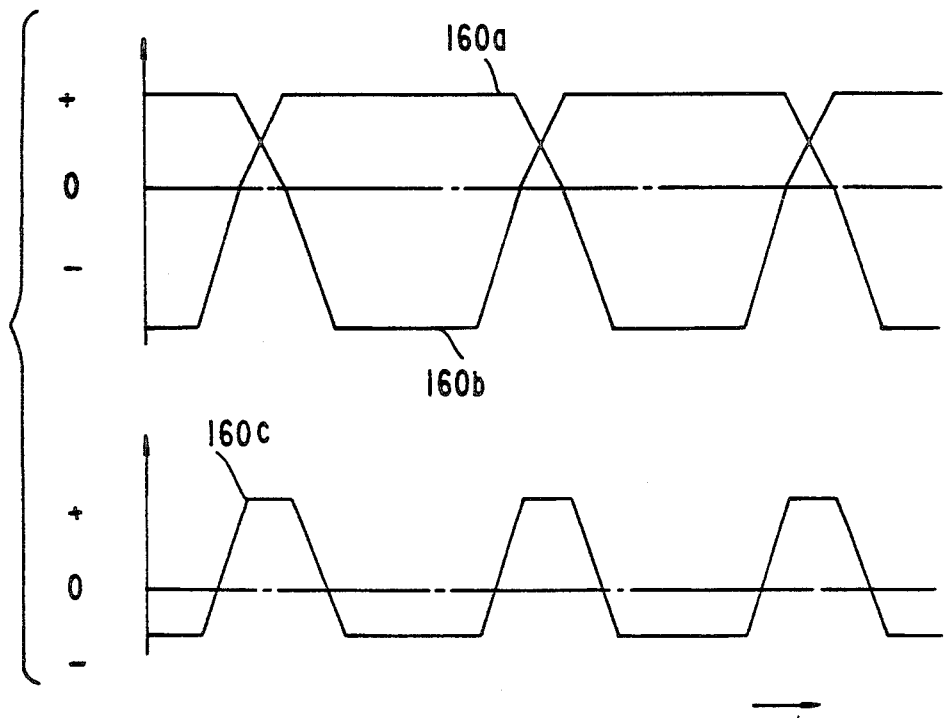
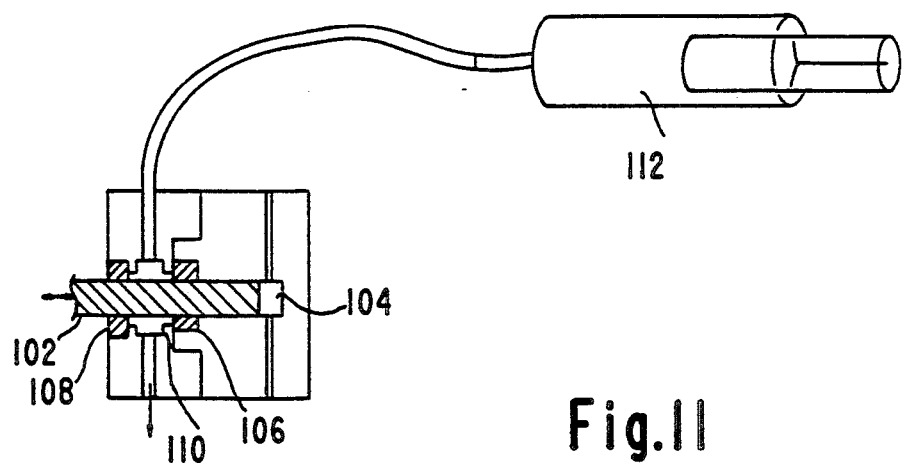
Fig.11
PRIOR ART

RECIPROCATING TYPE FLUID DELIVERY PUMP

This application is a continuation-in-part of application Ser. No. 255,570, filed Oct. 11, 1988, now abandoned.

BACKGROUND OF THE INVENTION

1. Field of the Invention

The present invention relates to a relatively small-volume fluid delivery pump wherein two plungers reciprocate to deliver a fluid; i.e, a so-called small-volume plunger reciprocating type fluid delivery pump which may be used, for example, to deliver a mobile phase in liquid chromatography.

2. 2. Description of the Related Art

A typical conventional small-volume plunger reciprocating type fluid delivery pump has a driving motor, plungers for driving two pump heads, respectively, and a converting mechanism for converting the rotational motion of the driving motor into a reciprocating motion of each plunger.

FIG. 4 shows the plunger speed characteristics with respect to an angle $\theta$ of a conventional small-volume plunger reciprocating type fluid delivery pump having two pump heads.

The curve 1 shows the plunger speed characteristics of the first pump head, while the curve 2 shows the plunger speed characteristics of the second pump head. A cam is used as a converting mechanism for converting the rotational motion of the driving motor into a reciprocating motion of each plunger. The axis of ordinates, i.e., $dr/d\theta$ (r is the distance from the center of rotation of the cam), represents the plunger speed at the time when the driving motor is rotating at a constant velocity. The upper and lower sides of the axis of abscissas show the plunger speeds at the deliver and suction sides, respectively.

The cam is shaped such that $dr/d\theta$ shows a trapezoidal pattern.

In the case of an ideal fluid whose delivery flow rate is proportional to the delivery-side plunger speed, the flow rate of the fluid being delivered, which is the sum of the respective delivery flow rates of the two pump heads, is constant throughout all angles of the cam when the driving motor is rotated at constant velocity, as shown by the reference numeral 3 in FIG. 4.

In practice, however, it is impossible to deliver a fluid at the beginning of the trapezoidal delivery cycle if the pressure is excessively high due to the compressibility of the fluid, the delay in response of a check valve and other factors, and deficiencies 4 and 5 occur in the delivery flow rate and the pressure as shown in FIG. 5. The result is a periodic pulsing flow which leads to a noise in a detection which must be carried out with a high sensitivity.

In order to reduce pulsations in the delivery of fluids, it is conventional practice to control the speed of rotation of the driving motor such that, during the beginning of delivery where the pressure may be insufficient the motor is rotated faster than in the other periods of the cycle.

More specifically, U.S. Pat. No. Re. 31,608, Magnusse Jr., discloses a fluid pump mechanism for delivering fluid against a back pressure which comprises a piston movable within a chamber for drawing fluid into the chamber during a chamber filling interval, pressurizing the fluid during a pressurizing interval wherein the fluid pressure attains an effective delivery value prior to delivery from the chamber and delivering the pressurized fluid from the chamber during a delivery interval of piston movement, and means for controlling the rate of piston movement such that the piston moves at a predetermined rate during delivery of the pressurized fluid. The controlling means includes a "pump-up" means for establishing a greater rate of piston movement during the pressurizing of the fluid, for signaling completion of fluid pressurization, and for thereupon establishing the predetermined rate of piston movement for effecting delivery of the pressurized fluid from the chamber, thereby increasing the time during which fluid is delivered to a receiving system and decreasing the time of filling or refilling and pump-up prior to such delivery, and thus enabling fluid to be delivered at a given flow rate and with a greatly reduced pulsation.

U.S. Pat. No. 4,045,343, Achener et al., discloses a high pressure liquid chromatography system including a reservoir for a liquid mobile phase, an LC column and detector, a high pressure reciprocating pump for enabling flow from the reservoir through the column, and a positively actuated inlet valve for controlling flow from the reservoir to the pump chamber. The pump is driven by motor means, such as a stepping motor, directly coupled thereto; and the inlet valve is actuated by the power train of the motor and pump, e.g., by an eccentric carried by the pump crank shaft. The pump piston is similarly driven by an eccentric, the pump and inlet valve eccentrics being angularly displaced in their respective positions at the crank shaft, as to delay opening of the inlet valve for a predetermined period following a pump stroke, in order to enable decompression of the liquid in the pump chamber. The average rotational velocity of the stepping motor is controlled throughout each full crank shaft rotation, so as to enable a precisely selected cycle of pump operation. In particular, the speed of the motor is so regulated in conjunction with the mechanical actuation of the pump piston and inlet valve as to provide (at the low flow rates where such behavior is critical) a very short duration fill period—which implies a rapid withdrawal of the piston or plunger from the pump cylinder. Thereafter, the second portion of the pumping cycle, which corresponds to pumping or displacing the liquid from the pump toward the chromatographic column, is effected under crank shaft rotation (as a function of time) such that the axial displacement of the piston is relatively linear as a function of time.

FIG. 6(A) shows compensation for pulsations in the case where a fluid is delivered under high pressure, while FIG. 6(B) shows pulsation compensation in the case where the delivery of a fluid is effected under low pressure. The reference symbol a represents a pulsing flow in the case where the speed of rotation of the cam is kept constant; b represents the speed of rotation of the cam controlled so as to compensate the pulsing flow; and c represents the pulsing flow thus compensated.

The higher the pressure, the greater the deficiency in pressure; therefore, as the pressure is increased, the rotational speed of the driving motor must be increased correspondingly.

Thus, the prior art method wherein the rotational speed of the driving motor is varied to reduce pulsations suffers from the problem that, as the pressure is increased, the rotational speed of the driving motor must be increased correspondingly to make compensation, and therefore the load on the motor increases and a driving motor having a relatively high output is needed.

A piston pump has a pump chamber having an inlet check valve and an outlet check valve in order to allow liquid to be pressurized to flow in one direction. A piston reciprocally moves within a pump chamber so that the liquid can be made to flow. A pump chamber seal partially surrounds the piston in order to prevent the liquid from leaking from the pump chamber. This means that the piston reciprocates with the rubbing of the pump chamber seal constantly. Although a pump chamber seal is provided, leaking by a small amount of liquid from the seal cannot be avoided due to the above-described mechanism.

In a liquid chromatograph, sometimes salt solution, such as, potassium phosphate water solution is conducted by the pump. When salt solution leaks from the pump chamber seal, the salt crystallizes on the backside of the seal over a long period of time, and, the crystallized salt tends to scratch the seal and detrimentally affects the pump's performance.

A pump which has a rinse chamber adjacent to a pump chamber is known. Water is supplied through the rinse chamber, thereby preventing salt crystallization on the seal. FIG. 11 shows such a pump which is provided with the rinse chamber.

Referring to FIG. 11, a piston 102 reciprocates within pump chamber 104. A pump chamber seal 106 partially surrounds the piston 102. A rinse chamber 110 is provided and includes a pump chamber seal 106 and a rinse chamber seal 108. The rinse chamber 110 has an inlet conduit and an outlet conduit. A syringe is connected to the inlet conduit. Water for rinsing is supplied by the syringe 112. Also, a chromatographic pump equipped with another pump for the rinse solution, instead of the syringe as shown in FIG. 11, is known.

However, a liquid chromatographic pump which has a rinse chamber equipped with a syringe for rinse water cannot regularly rinse a piston and a seal. Similarly, the liquid chromatographic pump which has a rinse chamber equipped with another pump for rinse water is fairly expensive.

SUMMARY OF THE INVENTION

In view of the above-described circumstances, it is a primary object of the present invention to provide a reciprocating type fluid delivery pump which is so designed that it is possible to compensate for pulsations occurring due to the compressibility of a fluid and other factors during the delivery starting period in a state wherein no load is applied to the driving motor.

To this end, the present invention provides a reciprocating type fluid delivery pump having a driving motor, plungers for driving two pump heads, respectively, and a converting mechanism for converting the rotational motion of the driving motor into a reciprocating motion of each plunger, wherein the converting mechanism includes a cam having such a configuration that, when the driving motor is rotated at constant velocity, the delivery flow rate during the delivery starting period of each of the plungers is in excess of that during the other periods of the cycle, and the speed of rotation of the driving motor is reduced during the excess delivery period according to need.

By virtue of the above-described arrangement, in such an ideal state that the flow rate of a fluid being delivered is proportional to the delivery-side speed of a plunger, if the driving motor is rotated at constant velocity, the delivery flow rate during the delivery starting period of the plunger is in excess of that during the other periods of the cycle. In the case where an ordinary fluid is delivered under high pressure, a deficiency in the delivery flow rate occurs during the delivery starting period due to the compressibility of the fluid and other factors. Therefore, the deficiency is canceled by the excess that is provided on the basis of the configuration of the cam.

In the case where a fluid is delivered under low pressure, if the driving motor is rotated at a constant velocity, the excess in the delivery flow rate that is provided by virtue of the cam configuration remains, so that the fluid is delivered to an excess. Therefore, the rotational speed of the cam is reduced during the excess delivery period so that the delivery flow rate is maintained at a constant level.

It is a further object of this invention to provide a liquid chromatographic pump which has a rinse pump which uses the reciprocal movement of the piston for the rinse pump mechanism so as to provide consistent rinsing whenever the liquid chromatographic pump is operated.

It is further an object of this invention to provide a liquid chromatographic pump equipped with a rinse pump which is economical, yet sturdy in construction and highly efficient in operation.

The aforementioned and other objects of the present invention are accomplished by providing a reciprocal piston pump having a rinse chamber with one wall being a pump chamber seal and another facing wall having a diaphragm which can reciprocally move together with the piston. The rinse chamber has an inlet check valve and an outlet check valve so that rinse water therein flows through in on direction.

More particularly, this invention includes a reciprocal piston pump with more than two pistons and pump chambers having the rinse chamber adjacent thereto. The conduit for each rinse chamber are connected in series so that the volume change of the rinse chambers, due to the reciprocal movement of the diaphragm, as a whole, is lower than when a single rinse chamber is employed due to the diminishing effect of each diaphragm movement.

Taking, for example, a pump having one pump chamber with one rinse chamber, when the piston reciprocates to pressurize the liquid, a diaphragm on the rinse chamber reciprocates together with the piston so that the inner volume of the rinse chamber is changed. The rinse chamber has an inlet check valve and an outlet check valve; thus, the volume change causes the rinse water to flow. If salt included in the pressurized liquid leaks from a pump chamber seal, the leaking liquid is diluted by the rinse liquid which goes through the rinse chamber so that the crystallization of the salt is avoided.

When the reciprocal piston pump includes more than two pistons having the rinse chamber thereof, and the rinse chambers are connected in series with each other, the pistons move alternately in order that the outflow of the liquid to be pressurized becomes smooth and continuous. The diaphragms of the rinse chambers also move alternately so that there is a period when an outflow of one rinse chamber due to the volume decrease subtracts the volume increase of the other rinse chamber. As a whole, the amount of outflow of the rinse solution is small.

BRIEF DESCRIPTION OF THE DRAWINGS

The above and other objects, features and advantages of the present invention will become clear from the following description of the preferred embodiment thereof, taken in conjunction with the accompanying drawings, in which:

FIG. 1 is a chart showing the relationship between the plunger speed characteristics and the deliver flow rate at a time when the driving motor is rotated at constant velocity in accordance with one embodiment of the present invention;

FIGS. 3(A), 3(B) and 3(C) show the operations of one embodiment of the present invention under different pressures;

FIG. 10 is a graphic illustration of the volume change of each rinse chamber, and the total volume change of the summation of both rinse chambers; and FIG. 11 is a schematic view of a conventional chromatographic pump.

DESCRIPTION OF THE PREFERRED EMBODIMENTS

The present invention will be described hereinunder in detail with reference to the accompanying drawings.

Figure 2:
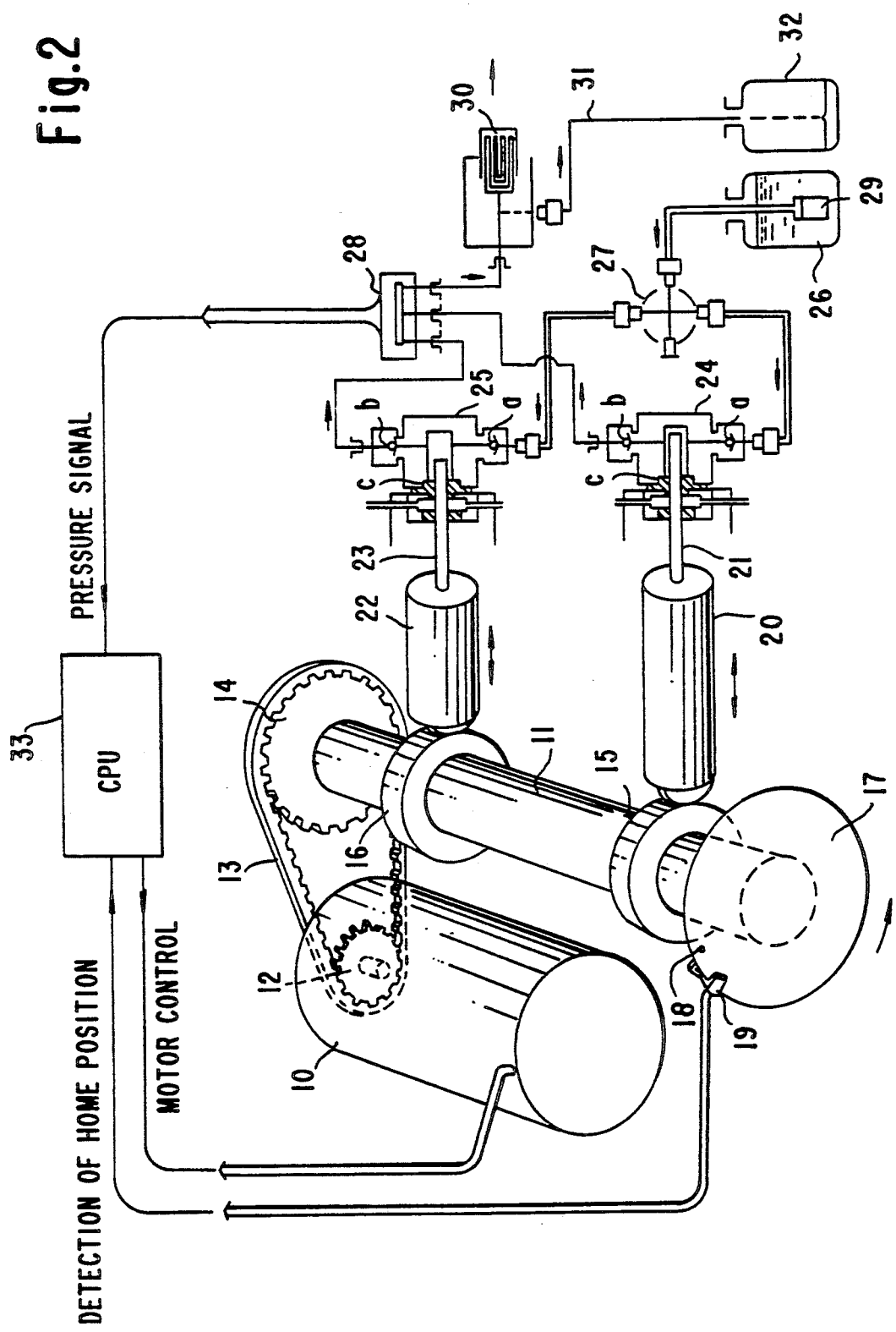
FIG. 2 shows the arrangement of one embodiment of the present invention.
Figure 4:
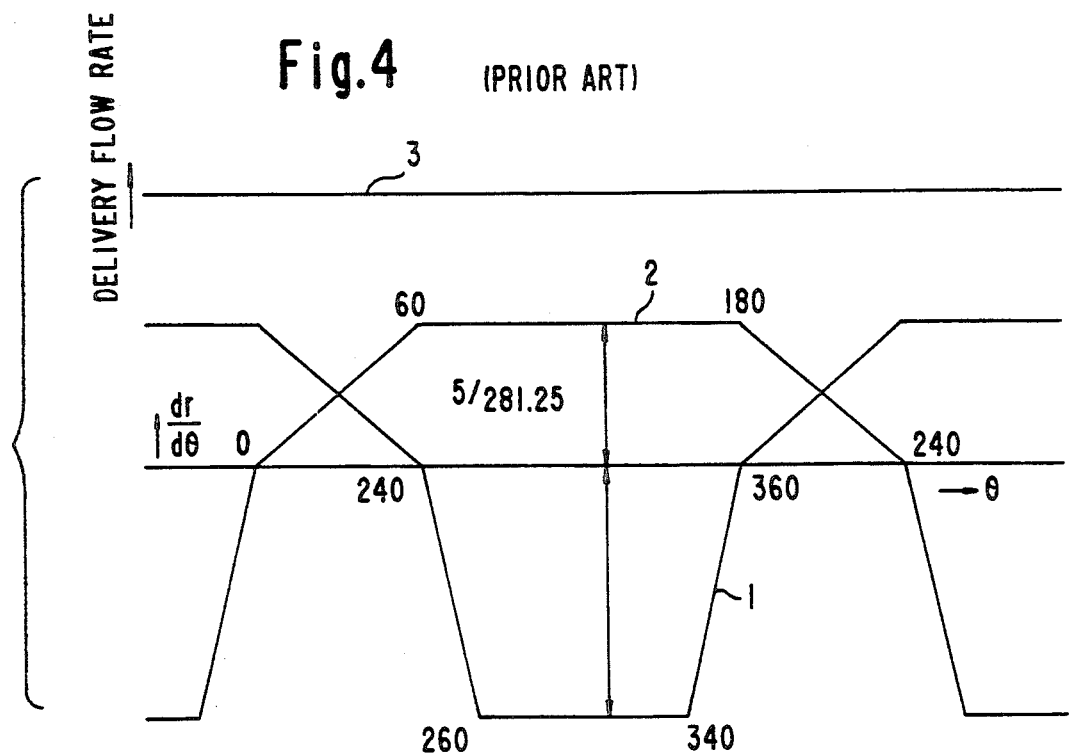
FIG. 4 is a chart showing the relationship between the plunger speed characteristics and the delivery flow rate at the time when the driving motor is rotated at a constant velocity in a conventional fluid delivery pump.
Figure 5:
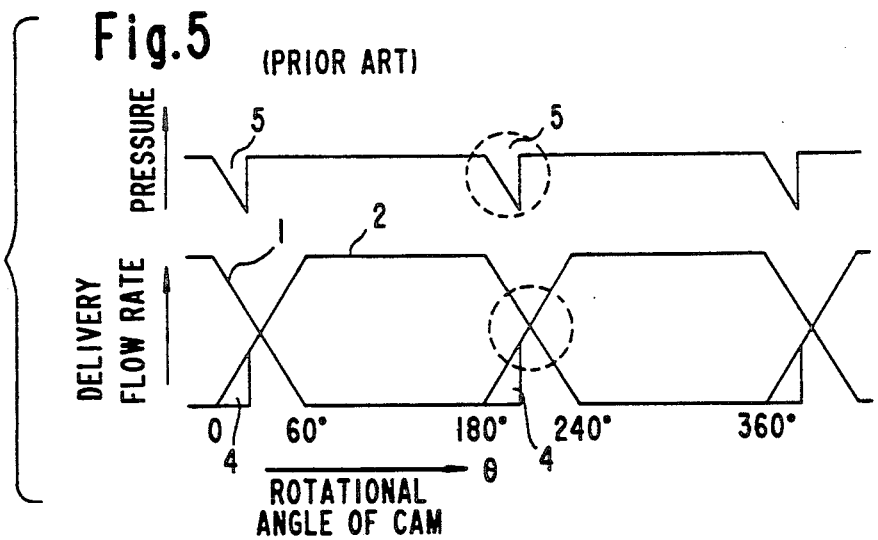
FIG. 5 is a chart showing the relationship between the delivery flow rate and pressure in the conventional fluid delivery pump.
Figure 6A:
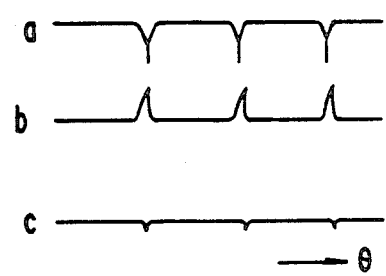
FIGS. 6(A) and 6(B) show the operations of the conventional fluid delivery pump under different pressures.
Figure 6B:
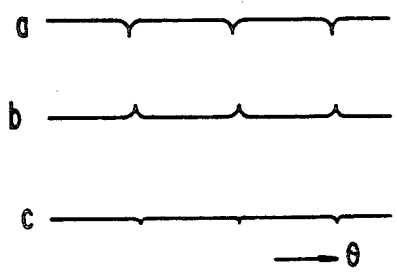

FIG. 2 shows a small-volume plunger reciprocating type fluid delivery pump to which the present invention is applied.

The reference numeral 10 denotes a driving stepping motor, and 11 a cam shaft 11 through a small pulley 12, a belt 13 and a large pulley 14 which is secured to the cam shaft 11.

The cam shaft 11 has two cams 15 and 16 secured thereto for driving two pump heads, respectively. The cam shaft 11 further has a disk 17 secured thereto. The disk 17 is provided with a bore 18, so that the home position relative to the rotational angle of the cam 15 and 16 is detected by detecting the bore 18 by means of a photocoupler 19.

The proximal end of a crosshead 20 is in contact with the cam 15 so that the crosshead 20 performs a reciprocating motion. A plunqer 21 of a first pump head 24 is secured to the other end of the crosshead 20. Similarly, the proximal end of a crosshead 22 is in contact with the other cam 16 so that the crosshead 22 performs a reciprocating motion, and a plunger 23 of a second pump head 25 is secured to the crosshead 22.

Cams 15 and 16, which will be described later in detail, are designed to have configurations that provide angle-plunger speed characteristics as shown in FIG. 1.

At the first pump head 24, the reciprocating motion of the plunger 21 causes a fluid 26 to be delivered to a flow path leading to a pressure sensor 28 from a suction filter 29 and an inlet block 27. At the second pump head 25 also, the reciprocating motion of the plunger 23 causes the fluid 26 to be delivered to a flow path leading to the pressure sensor 28 from the suction filter 29 and the inlet block 27. At each of the pump heads 24 and 25, the reference symbol a denotes an inlet check valve, b an outlet check valve, and c seal member.

In the pressure sensor 28, the fluids respectively delivered from the first and second pump heads 24 and 25 are joined together and are then delivered from a pump outlet 30 to a flow path which leads to a column. Reference numeral 31 denotes a drain flow path, and 32 a drain bin.

The reference numeral 33 denotes a CPU. A pressure signal from the pressure sensor 28 and a home position detecting signal from the photocoupler 19 are sent to CPU 33. CPU 33 controls the speed of rotation of the stepping motor 10.

The configurations of the cams 15 and 16 are determined so that the $dr/d\theta$ (the plunger speed at the time of uniform rotation) characteristics with respect to the cam rotational angle $\theta$ are set such as those shown in FIG. 1. In FIG. 1, the curves 1a and 2a represent the $dr/d\theta$ characteristics of the first and second pump heads, respectively.

The following is the cam configuration that provides the $dr/d\theta$ characteristics shown in FIG. 1.

| | |
|---|---|
| $0 < \theta \leq 10$ | $r = 15.5 + 0.75\theta^2/294.14062$ |
| $10 < \theta \leq 25$ | $r = 15.5 + (1.5\theta - 7.5)/294.14062$ |
| $25 < \theta \leq 70$ | $r = 15.5 + (7\theta^2/180 - 4\theta/9 + 605/36)/294.14062$ |
| $70 < \theta \leq 205$ | $r = 15.5 + (5\theta - 173.75)/294.14062$ |
| $205 < \theta \leq 220$ | $r = 15.5 + (-8\theta^2/90 + 373\theta/9 - 140735/36)/294.14062$ |
| $220 < \theta \leq 250$ | $r = 15.5 + (-7\theta^2/180 + 175\theta/9 - 53615/36)294.14062$ |
| $250 < \theta \leq 300$ | $r = 15.5 + (-0.1255\theta^2 + 62.75\theta - 6902.5)/294.14062$ |
| $300 < \theta \leq 340$ | $r = 15.5 + (-12.55\theta + 4392.5)/294.14062$ |
| $340 < \theta \leq 360$ | $r = 15.5 + (0.31375\theta^2 - 225.9\theta + 4066.2)/294.14062$ |

As shown in FIG. 1, if the driving motor is rotated at constant velocity, the sum of the respective speeds of the two plungers is larger during the delivery starting period of each plunger than during the other periods of the cycle. Therefore, assuming that the flow of the fluid accurately follows the delivery-side plunger speed, the delivery flow rate 3a goes to excess during the delivery starting period in each cycle, as shown by the reference symbol A.

FIGS. 3(A)–3(C) show the relationship between the pressure and the rotational speed of the driving motor in this embodiment.

FIG. 3(A) shows the pulsation compensation that is made in the case where fluid delivery is carried out under substantially no pressure. If the driving motor is rotated at constant velocity, excesses A occur in the delivery flow rate during the delivery starting period in each cycle, as shown by graph a. Therefore, the driving motor is decelerated such that the rotational speed of each cam is reduced during each delivery starting period, as shown by graph b. As a result, the delivery flow rate becomes constant as shown by graph c.

FIG. 3(B) shows the pulsation compensation that is made in the case where the fluid delivery is carried out under low pressure. If the driving motor is rotated at constant velocity, an excess A' in the delivery flow rate appears in the temporally latter portion of each excess delivery period, as shown by graph a. Therefore, the rotational speed of the motor is reduced as shown by graph b. As a result, the delivery flow rate becomes constant as shown by graph c.

FIG. 3(C) shows the pulsation compensation made in the case where the fluid delivery is carried out under high pressure. In this case, deficiencies in the delivery flow rate due to high pressure and excesses in the delivery flow rate due to the modification of the cams cancel each other, so that the delivery flow rate in graph a at the time when the driving motor is rotated at constant velocity is constant. Accordingly, there is no need to compensate the rotational speed in graph b of the driving motor.

Since the relationship between the pressure and the optimal amount of compensation (i.e., the driving motor deceleration period) depends on the kind of fluid delivered, it may be possible to set the relationship in advance or obtain it automatically while monitoring the level of the pressure.

The compensation that is made by decelerating the driving motor is conducted in a relatively low flow rate region where it is highly essential to reduce pulsations. In flow rate regions where the flow rate is high and fluid delivery is effected at high frequency, pulsations are small, so that it is unnecessary to reduce the rotational speed of the driving motor to compensate. In such a case, the cams may be rotated at constant velocity.

In the present invention, the configurations of cams for reciprocating respective plungers are improved so that, when the driving motor is rotated at constant velocity, the delivery flow rate during the delivery starting period of each of the plungers is in excess of that during the other periods of the cycle. Therefore, the speed of rotation of the driving motor is controlled in such a manner that, when the fluid is delivered under low pressure, the rotational speed is reduced, whereas, when the fluid delivery is carried out under high pressure, the motor is rotated at constant velocity. Accordingly, the load on the driving motor is reduced and it is possible to employ a driving motor having a relatively low output in comparison with the conventional compensation wherein the rotational speed of the driving motor is increased under high pressure.

Figure 7:
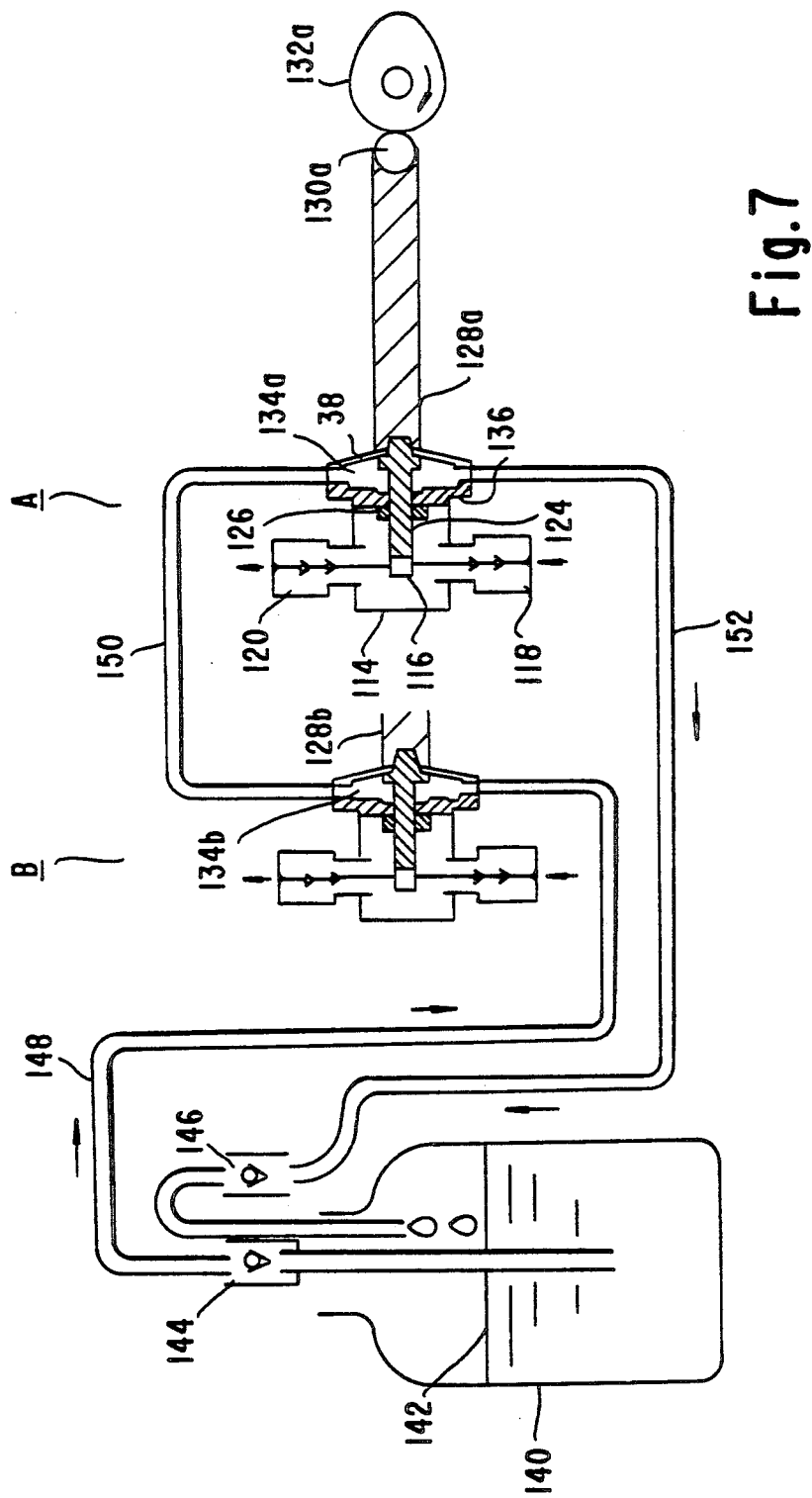
FIG. 7 is a schematic view of an embodiment of this invention.

FIG. 7 shows another embodiment of the present invention. The liquid chromatographic pump of this invention has two cylinder blocks A and B. There are rinse chambers 134a, 134b which are connected in series with each other by a tube 150.

As shown in the cylinder block A in FIG. 7, a pump chamber 116 has an inlet conduit and an outlet conduit, while the inlet conduit has an inlet check valve 118 and the outlet conduit has an outlet check valve 120. Liquid to be pressurized flows from the inlet check valve 118 through the pump chamber 116 to the outlet check valve 120. A piston 124 which is partially surrounded by a pump chamber seal 126, reciprocates within the pump chamber 116 while rubbing the pump chamber seal 126. The piston 124 is installed at one end of a push rod 128a, while a cam follower 130a is installed at the other end of the push rod 128a. The cam follower 130a faces a cam 132a.

The cylinder block B has the same structure as the cylinder block A. A push rod 128b has a cam follower which faces a cam which is not shown in FIG. 7. The cam 132a for moving the push rod 128a and the cam for moving the push rod 128b are installed with the same cam rod, and the cam rod is rotated by one motor.

The pump includes the rinse chambers 134a, 134b. Referring now to the rinse chamber 134a, the rinse chamber 134a has two walls. One wall is a cylinder holder 136 which contacts the pump chamber seal 126, while the other wall is a diaphragm 138 having a center portion which is connected to push rod 130a, and having a periphery which is connected to the cylinder holder 136 and basement 162 (shown and described in more detail below with reference to FIG. 8). The rinse chamber 134b has the same structure as the rinse chamber 134a.

Rinse liquid 142 inside a liquid bottle 140 flows through an inlet check valve, an inlet conduit 148, the rinse chamber 134b, a tube 150, the rinse chamber 134a, an outlet conduit 152, and an outlet check valve 146, then returns to the liquid bottle 140.

Figure 8:
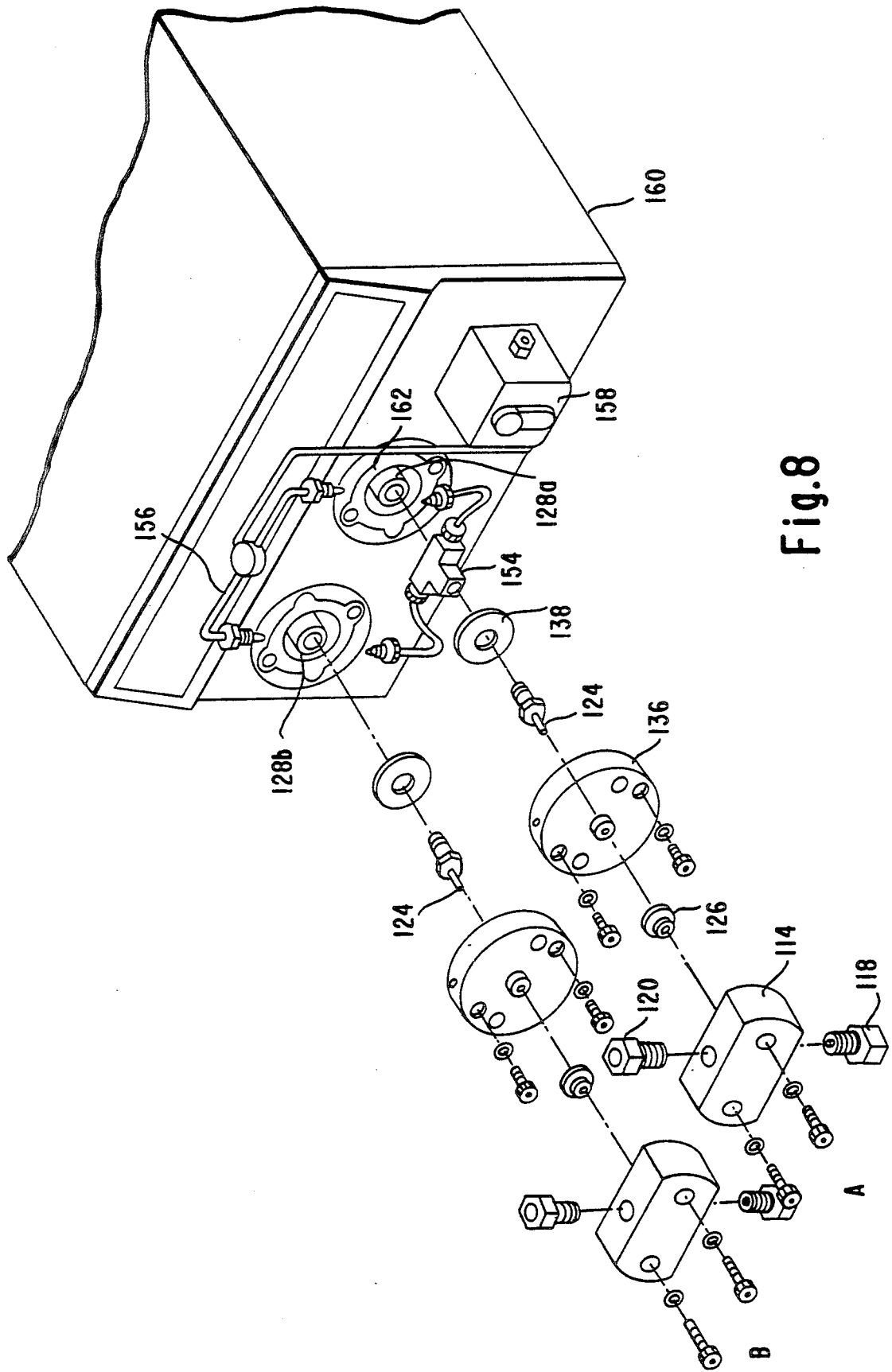
FIG. 8 is an exploded perspective view of cylinder heads used in this invention.

FIG. 8 shows the cylinder heads A and B, and the rinse chambers 134a, 134b in more detail. The piston 124 has a male screw at one end thereof, and the push rod 128 has a female screw at one end thereof. The diaphragm 138 has a circular shape with a center hole, and with the center hole which is between the piston 124 and the push rod 128. The periphery of the diaphragm is fixed between the cylinder holder 136 and the basement 162. The piston 124 goes through a center hole of the cylinder holder 136 and the pump chamber seal 126, and is arranged inside the pump chamber.

An inlet conduit connector 154 is connected to the inlet check valves 118 by tubes, and an outlet conduit connector 156 is connected to the outlet check valves 120 tubes. A pressure transducer 158 is connected to an outlet tube. Inside a pump housing 160, there are cams and a motor for rotating the cams.

Figure 9:
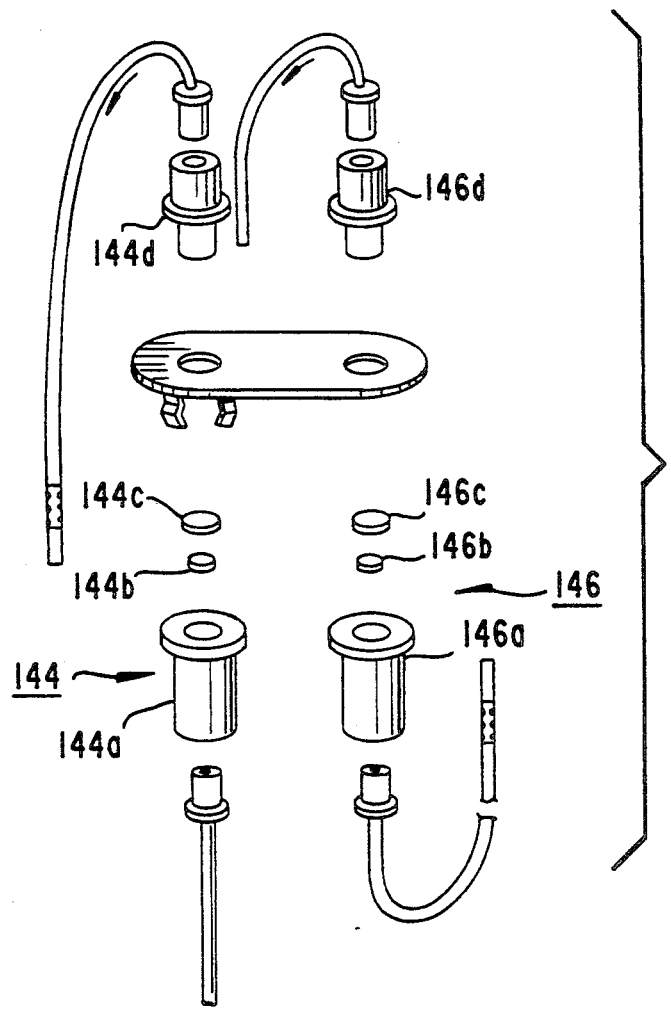
FIG. 9 is an exploded perspective view of check valve assemblies employed in this invention.

FIG. 9 shows in more detail the construction of the check valve assemblies 144, 146 for the rinse solution flow. As shown in FIG. 9, each of the check valve assemblies 144, 146 includes a housing 144a which has a seat holder therein, and receives an inlet tube, a plate 144b, a plate stopper 144c and an inner housing which receives an outlet tube. The plate 144b can move between the seat and the plate stopper 144c so that liquid flows therethrough in one direction; i.e., upward as shown in FIG. 9.

The operation of the piston pump will now be described with reference to FIGS. 7 and 10.

Starting with the cylinder block A, the piston 124 reciprocates by rotating the cam 132a, while the inner volume of the pump chamber 116 changes constantly so that the liquid to be pressurized flows from the inlet check valve 118 to the outlet check valve 120.

Since the diaphragm 138 is fixed on the push rod 128, the inner volume of the rinse chamber constantly changes along with the reciprocal movement of the diaphragm 138 and the push rod 128. When the push rod 128, as shown in FIG. 7, slides towards the right, and the inner volume of the rinse chamber increases, the rinse solution is sucked to the rinse chamber. When the push rod 128 slides towards the left, and the inner volume of the rinse chamber decreases, the rinse solution is delivered from the rinse chamber.

As shown in FIG. 7, the liquid chromatographic pump has two cylinder heads and thus, two rinse chambers. The two rinse chambers are connected in series with each other. FIG. 10 shows the volume change of each rinse chamber, and the total volume change of the summation of both rinse chambers which is a result of the series connection of the two rinse chambers. In FIG. 10, a graph 160a shows the volume change of the rinse chamber 134a, a graph 160b shows the volume change of the rinse chamber 134b, and a graph 160c shows the volume change of the summation of both rinse chambers.

A result of the alternate movement of the push rods 128a, 128b, the volume change of each rinse chamber cycles alternately. The summation volume change 160c results in one forth of each volume change of one rinse chamber. Since there is no check valve between the two rinse chambers, and there is a relatively large inner volume in the conduit between the check valves and the rinse chambers, the volume change of one rinse chamber reduces the volume change of the other rinse chamber.

The present invention is similarly applicable to a pump which has more than three cylinder heads or one cylinder head.

The present invention provides a liquid chromatographic pump which, when in operation, operates a rinse pump in order to prevent crystallization of salt on the backside of the pump chamber seal.

When the present invention has more than two pumps, the flow rate of the rinse solution can be reduced which in turn reduces the load to the pump drive motor, thereby prolonging the life of the diaphragm.

While the invention has been particularly shown and described in reference to preferred embodiments thereof, it will be understood by those skilled in the art that changes in form and details may be made therein without departing from the spirit and scope of the invention.

What is claimed is:

1. A reciprocating type fluid delivery pump with two pump heads arranged for parallel flow of fluid output therefrom, comprising:
   a driving motor;
   a pair of plungers for driving said two pump heads, respectively, each plunger reciprocable within a pump chamber of one of said two respective pump heads, wherein each pump chamber has a pump chamber seal for reducing leakage around a respective one of said plungers;
   a converting means for converting the rotational motion of said driving motor into reciprocating motion of each plunger, wherein said converting means includes a pair of cams, wherein each cam engages with a corresponding one of said plungers for reciprocating said plungers to provide a delivery flow rate of fluid from each plunger, during a delivery starting period, which is in excess of a delivery flow rate during other periods of each plunger cycle when said driving motor is rotated at a constant velocity when fluid delivery is not carried out under high pressure, and when the fluid delivery is carried out under high pressure, the delivery flow rate is substantially constant when said driving motor is rotated at a constant velocity, and wherein each cam has a shape such that, during the delivery starting period, each cam drives its corresponding plunger to have only and increasing or constant plunger speed;
   a means for selectively decelerating and driving motor during said excess delivery period when fluid delivery is not carried out under high pressure; and
   a rinsing means, housed within one of said pump heads, for preventing crystallization of a salt on a rear portion of said pump chamber seal of said one pump head, wherein said rinsing means includes at least one rinse chamber having an inner volume which constantly changes for conducting rinsing fluid therethrough.

2. The reciprocating type fluid delivery pump of claim 1, wherein said rinse chamber includes a first wall in contact with said pump chamber seal, and an opposing second wall being a diaphragm, said second wall operatively connected to a portion of a respective one of said plungers.

3. The reciprocating type fluid delivery pump of claim 2, wherein said rinse chamber includes inlet and outlet conduits, each operatively coupled with a check valve connected to a source of said rinsing liquid, such that the movement of said diaphragm, in response to the reciprocation of said plunger, causes the rinsing liquid to be pumped through the rinse chamber.

4. The reciprocating type fluid delivery pump of claim 1, wherein said rinse chamber of one pump head and another rinse chamber of another one of said pump heads are connected in series.

5. The reciprocating type fluid delivery pump as in claim 4, wherein an outlet conduit of said rinse chamber of one pump head is connected to an inlet conduit of another rinse chamber of another one of said pump heads for allowing said pressurized liquid to pass through in series between said rinse chambers.

* * * * *